US009128249B2

(12) United States Patent
Hasegawa et al.

(10) Patent No.: US 9,128,249 B2
(45) Date of Patent: Sep. 8, 2015

(54) OPTICAL PROBE AND OPTICAL MEASURING METHOD

(71) Applicant: Sumitomo Electric Industries, Ltd., Osaka-shi (JP)

(72) Inventors: Takemi Hasegawa, Yokohama (JP); Mitsuharu Hirano, Yokohama (JP)

(73) Assignee: Sumitomo Electric Industries, Ltd., Osaka-shi (JP)

( * ) Notice: Subject to any disclaimer, the term of this patent is extended or adjusted under 35 U.S.C. 154(b) by 0 days.

(21) Appl. No.: 14/234,040

(22) PCT Filed: Mar. 14, 2013

(86) PCT No.: PCT/JP2013/057139
§ 371 (c)(1),
(2) Date: Jan. 21, 2014

(87) PCT Pub. No.: WO2013/141128
PCT Pub. Date: Sep. 26, 2013

(65) Prior Publication Data

US 2014/0158888 A1 Jun. 12, 2014

(30) Foreign Application Priority Data

Mar. 21, 2012 (JP) ................................ 2012-063984

(51) Int. Cl.
*G01J 5/02* (2006.01)
*G02B 6/32* (2006.01)
(Continued)

(52) U.S. Cl.
CPC ................ *G02B 6/32* (2013.01); *A61B 5/0066* (2013.01); *A61B 5/0073* (2013.01);
(Continued)

(58) Field of Classification Search
CPC .. G02B 6/0218; G02B 6/2558; G02B 6/4432; C03B 2201/86; C03B 2203/12; C03B 2203/14; C03B 2203/16; C03B 2203/18; C03B 2203/142; B29D 11/00663
USPC ........................................................ 250/347
See application file for complete search history.

(56) References Cited

U.S. PATENT DOCUMENTS 4,648,168 A * 3/1987 Nolf et al. .................... 385/135
5,452,394 A * 9/1995 Huang ......................... 385/123
(Continued)

FOREIGN PATENT DOCUMENTS

JP 2002-263106 A 9/2002
JP 2004-223269 A 8/2004
(Continued)

OTHER PUBLICATIONS

R.E. Schuh, et al., "Theoretical analysis and measurement of effects of fibre twist on polarisation mode dispersion of optical fibres," Electronics Letters, vol. 31, No. 20, pp. 1772-1773 (1995).
(Continued)

*Primary Examiner* — Kiho Kim
(74) *Attorney, Agent, or Firm* — Venable LLP; Michael A. Sartori; F. Brock Riggs

(57) ABSTRACT

An optical measurement method that can suppress variation in detection sensitivity even if an optical probe is bent, and an optical probe suitably used for the method are provided. An optical probe 10 includes an optical fiber 11 that transmits light between a proximal end **11*a* and a distal end 11*b*, an optical connector 12 connected with the optical fiber 11 at a side of the proximal end 11*a*, a focusing optical system 13 and a deflecting optical system 14 optically connected with the optical fiber 11 at a side of the distal end 11*b*, and a support tube 15 and a jacket tube 16 surrounding the optical fiber 11 and extending along the optical fiber 11. The optical fiber 11 is twisted by a number of turns in a range from one turn/m to 50 turns per meter around an axis of the optical fiber as the center and fixed relative to the support tube 15**.

5 Claims, 4 Drawing Sheets

1 10 38 30 11a 31 32 12 33 36 34 35 37 11b 13 14 11 15 16 3

(51) Int. Cl.

| | |
|---|---|
| ***A61B 5/00*** | (2006.01) |
| ***G01B 9/02*** | (2006.01) |
| *A61B 5/02* | (2006.01) |

(52) U.S. Cl.

CPC ............ *A61B 5/0075* (2013.01); *A61B 5/0086* (2013.01); *G01B 9/0205* (2013.01); *G01B 9/02091* (2013.01); *A61B 5/02007* (2013.01)

(56) References Cited

U.S. PATENT DOCUMENTS

| | | | | |
|---|---|---|---|---|
| 5,740,295 | A * | 4/1998 | Kinard et al. | 385/109 |
| 6,445,939 | B1 | 9/2002 | Swanson et al. | |
| 8,280,212 | B2 * | 10/2012 | Goell et al. | 385/123 |
| 2002/0151823 | A1 | 10/2002 | Miyata et al. | |
| 2007/0053640 | A1 * | 3/2007 | Goell et al. | 385/123 |
| 2010/0282970 | A1 * | 11/2010 | Haran et al. | 250/339.07 |
| 2011/0058768 | A1 * | 3/2011 | Swinehart et al. | 385/13 |

FOREIGN PATENT DOCUMENTS

| | | | |
|---|---|---|---|
| JP | 2007-206049 | A | 8/2007 |
| JP | 2008-142443 | A | 6/2008 |
| JP | 2011-524003 | A | 8/2011 |

OTHER PUBLICATIONS

R. Ulrich, et al., "Bending-induced birefringence in single-mode fibers," Optics Letters, vol. 5, No. 6, pp. 273-275 (1980).

M. Legre, et al., "Investigation of the Ratio Between Phase and Group Birefringence in Optical Single-Mode Fibers," Journal of Lightwave technology, vol. 21, No. 12, pp. 3374-3378 (2003).

International Search Report in PCT International Application No. PCT/JP2013/057139, dated Jun. 18, 2013.

* cited by examiner 1
10
11a
12
11
15
16
11b
13
14
3
30
31
32
33
34
35
36
37
38

14
13
11b
17
11
11d
11c
16
15
12
11a
10
CW

OPTICAL PROBE AND OPTICAL MEASURING METHOD

TECHNICAL FIELD

The present invention relates to an optical probe that is used for measuring a tomographic structure of the lumen of an object such as a blood vessel with a luminal shape by using a method of optical coherence tomography (OCT).

BACKGROUND ART

U.S. Pat. No. 6,445,939 describes OCT as a method of measuring a tomographic structure of the lumen of an object with a luminal shape, and an optical probe that is inserted into the lumen of the object and used for the OCT measurement. For the OCT measurement, a graded-index optical fiber connected with a tip end (a distal end) of a single-mode optical fiber functions as a lens, and is configured to have a working distance larger than 1 mm and a spot size smaller than 100 μm. Accordingly, an object having an inner radius larger than 1 mm can be optically measured with a spatial resolution smaller than 100 μm.

In the OCT measurement, light output from a light source is branched into two of illumination light and reference light. An optical probe irradiates an object with the illumination light, guides backward reflection light, which is generated at the object as the result of the irradiation, to an optical detector, and also guides the reference light to the optical detector. Then, the optical detector detects interference light of the backward reflection light and the reference light. An analyzing part analyzes a spectrum of the backward reflection light, and acquires distribution information of a substance in the object as image information.

SUMMARY OF INVENTION

Technical Problem

An object of the invention is to provide an optical measurement method that can suppress variation in detection sensitivity even if an optical probe is bent, and an optical probe suitably used for the method.

Solution to Problem

An optical probe according to the invention includes (1) an optical fiber that transmits light between a proximal end and a distal end; (2) an optical connector connected with the optical fiber at a side of the proximal end; (3) a focusing optical system having one end connected with the optical fiber at the distal end, the focusing optical system focusing the light emitted from the distal end of the optical fiber; (4) a deflecting optical system optically connected with the optical fiber at a side of the distal end, the deflecting optical system deflecting the light emitted from the distal end of the optical fiber; (5) a support tube surrounding the optical fiber, extending along the optical fiber, fixed relative to the optical connector at the side of the proximal end, and fixed relative to either of the optical fiber, the focusing optical system, and the deflecting optical system at the side of the distal end; and (6) a jacket tube surrounding the support tube, extending along the support tube, and being rotatable relative to the optical fiber, the optical connector, the focusing optical system, the deflecting optical system, and the support tube. Further, the optical fiber is twisted by a number of turns (a pitch) in a range from one turn per meter to 50 turns per meter around an axis of the optical fiber as the center and fixed to the support tube.

One end of the deflecting optical system may be connected with the other end of the focusing optical system. Alternatively, a graded index (GI) lens with one end thereof being obliquely cut may form both the focusing optical system and the deflecting optical system.

In the optical probe of the invention, the support tube may have a structure in which a plurality of linear bodies are stranded and twisted, and in a free state in which rotation is not introduced from the connector, a twist direction of the optical fiber and a twist direction of the support tube may be opposite to each other.

An optical measurement method according to the invention implemented with the above-described optical probe, a light source that emits near infrared light, a polarization adjusting part that converts the near infrared light emitted from the light source into near infrared light in a circular polarization state and outputs the near infrared light, an optical branching part that branches the near infrared light output from the polarization adjusting part into two of illumination light and reference light and outputs the illumination light and the reference light, an optical detector that detects the near infrared light, and an analyzing part that analyzes an attenuation spectrum of the near infrared light and acquires the analysis result as image information, the method includes: irradiating an object with the illumination light which is output from the optical branching part, entered to the proximal end of the optical fiber, and emitted from the distal end of the optical fiber; guiding backward reflection light which is generated at the object as the result of the irradiation to the optical detector by causing the backward reflection light, entered to the distal end of the optical fiber, and emitted from the proximal end of the optical fiber, while guiding the reference light output from the optical branching part to the optical detector; detecting interference light of the backward reflection light and the reference light by the optical detector; and analyzing a spectrum of the backward reflection light by the analyzing part and acquiring distribution information of a substance in the object as the image information.

In the optical measurement method of the invention, the support tube may have a structure in which a plurality of linear bodies are stranded and twisted, in a free state in which rotation is not introduced from the connector, a twist direction of the optical fiber and a twist direction of the support tube may be opposite to each other, and the inside of the object may be scanned with the illumination light while the optical fiber, the optical connector, the focusing optical system, the deflecting optical system, and the support tube are rotated together in a direction opposite to the twist direction of the support tube. Also, the optical fiber may be twisted by a number of turns in a range from five turns per meter to 50 turns per meter by rotating the optical fiber, the optical connector, the focusing optical system, the deflecting optical system, and the support tube together.

Advantageous Effects of Invention

With the invention, variation in detection sensitivity can be suppressed even if the optical probe is bent.

DESCRIPTION OF EMBODIMENTS

Figure 1:
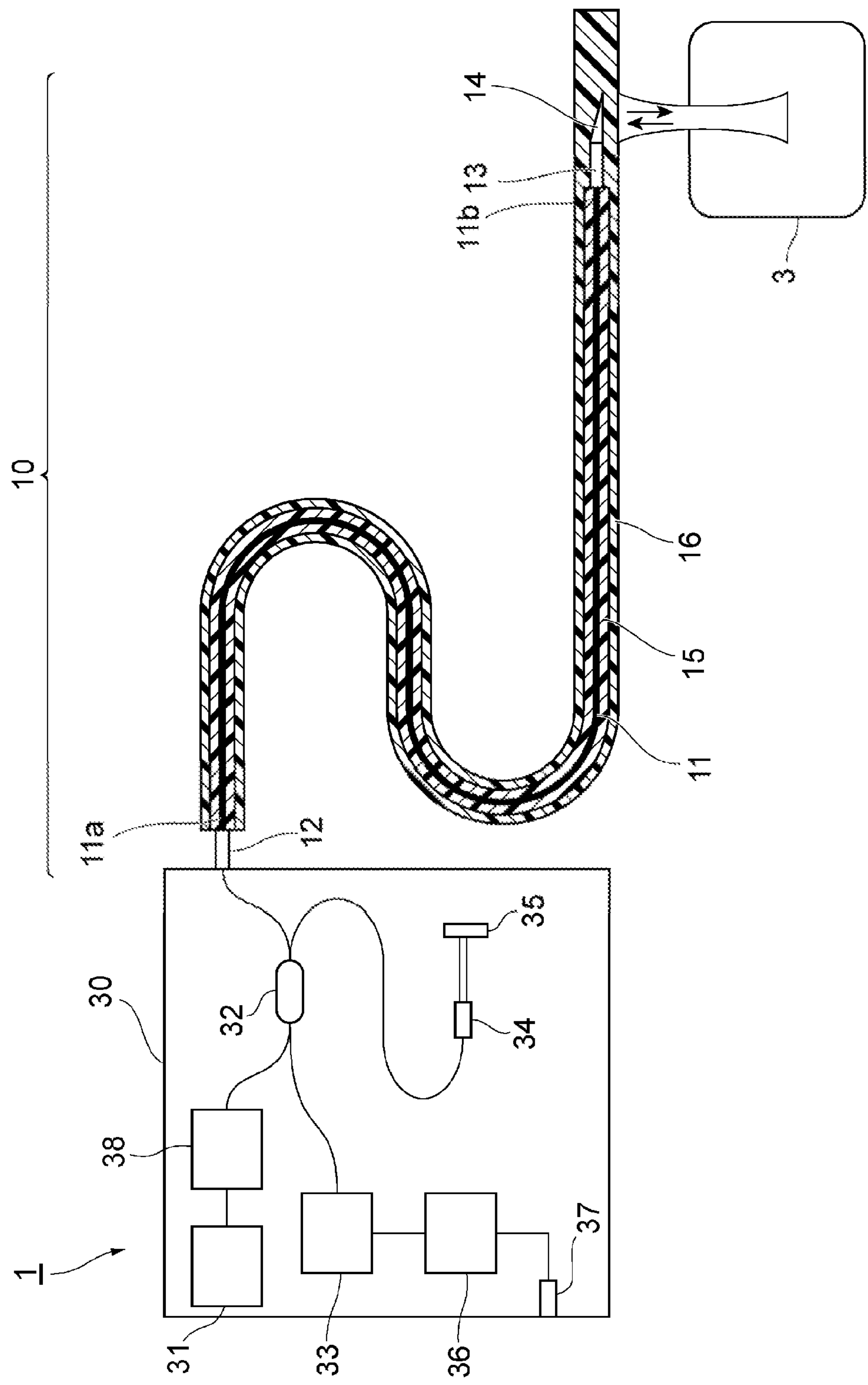
FIG. 1 is a conceptual diagram of an OCT instrument including an optical probe according to an embodiment of the invention.

An embodiment of the invention is described below with reference to the drawings. The drawings are provided for explanation, and do not intend to limit the scope of the invention. In the drawings, the same reference sign indicates the same part to avoid redundant description. The proportion of dimensions in each drawing may not be exact.

An OCT instrument using a conventional optical prove has had a problem in which if the optical probe is bent, a polarization state of illumination light and a polarization state of backward reflection light propagating through the optical probe varies and hence detection sensitivity varies. The problem could have been addressed by, for example, a method of detecting backward reflection light for each polarization state. However, an additional detector is required for the method, and the instrument cost is increased.

FIG. 1 is a conceptual diagram of an OCT instrument 1 including an optical probe 10 according to an embodiment of the invention. The OCT instrument 1 includes the optical probe 10 and a measuring unit 30, and acquires an optical coherence tomographic image of an object 3.

The optical probe 10 includes an optical fiber 11 that transmits light between a proximal end 11*a* and a distal end 11*b*, an optical connector 12 connected with the optical fiber 11 at a side of the proximal end 11*a*, a focusing optical system 13 and a deflecting optical system 14 optically connected with the optical fiber 11 at a side of the distal end 11*b*, and a support tube 15 and a jacket tube 16 surrounding the optical fiber 11 and extending along the optical fiber 11. The optical connector 12 is optically connected with the measuring unit 30.

The measuring unit 30 includes a light source 31 that emits near infrared light, a polarization adjusting part 38 that converts the near infrared light emitted from the light source 31 into near infrared light in a circular polarization state and outputs the near infrared light, an optical branching part 32 that branches the near infrared light output from the polarization adjusting part 38 into two of illumination light and reference light and outputs the illumination light and the reference light, an optical detector 33 that detects the light reaching from the optical branching part 32, an optical terminal 34 that outputs the reference light reaching from the optical branching part 32, a mirror 35 that reflects the reference light output from the optical terminal 34 to the optical terminal 34, an analyzing part 36 that analyzes a spectrum of the light detected by the optical detector 33, and an output port 37 that outputs the result of the analysis made by the analyzing part 36.

In the measuring unit 30, the light source 31 outputs the near infrared light in a linear polarization state, and the polarization adjusting part 38 converts the near infrared light into the near infrared light in the circular polarization state. The near infrared light in the circular polarization state output from the polarization adjusting part 38 is branched into two of the illumination light and the reference light by the optical branching part 32, and output as the illumination light and the reference light. The illumination light output from the optical branching part 32 is incident on the proximal end 11*a* of the optical fiber 11 through the optical connector 12, guided by the optical fiber 11, emitted from the distal end 11*b*, and illuminated on the object 3 through the focusing optical system 13 and the deflecting optical system 14. The backward reflection light generated in accordance with the irradiation on the object 3 with the illumination light is incident on the distal end 11*b* of the optical fiber 11 through the deflecting optical system 14 and the focusing optical system 13. Then, the light is guided by the optical fiber 11, emitted from the proximal end 11*a*, and coupled with the optical detector 33 through the optical connector 12 and the optical branching part 32.

The reference light output from the optical branching part 32 is emitted from the optical terminal 34, is reflected by the mirror 35, passes through the optical terminal 34 and the optical branching part 32, and is coupled with the detector 33. The backward reflection light from the object 3 interferes with the reference light at the optical detector 33. The optical detector 33 detects the interference light. The spectrum of the interference light is input to the analyzing part 36. The analyzing part 36 analyzes the spectrum of the interference light, and hence calculates the distribution of backward reflection efficiency at respective points in the object 3. The tomographic image of the object 3 is calculated on the basis of the calculation result.

The optical fiber 11, the focusing optical system 13, the deflecting optical system 14, and the support tube 15 of the optical probe 10 can rotate together in the jacket tube 16. With this rotation, the object 3 can be scanned with the illumination light. By calculating the reflectivity distribution of each portion of the object 3 with the illumination light, the tomographic image of the object 3 is calculated, and the tomographic image is output as an image signal from a signal output port 37.

A mechanism, in which the illumination light emitted from the distal end 11*b* of the optical fiber 11 reaches the object 3 and returns to the distal end 11*b* of the optical fiber 11 again, may include reflection, refraction, and scattering in strict sense. However, the difference among reflection, refraction, and scattering is not essential for the invention, and hence reflection, refraction, and scattering are collectively called backward reflection in the specification for simplifying the description.

Figure 2:
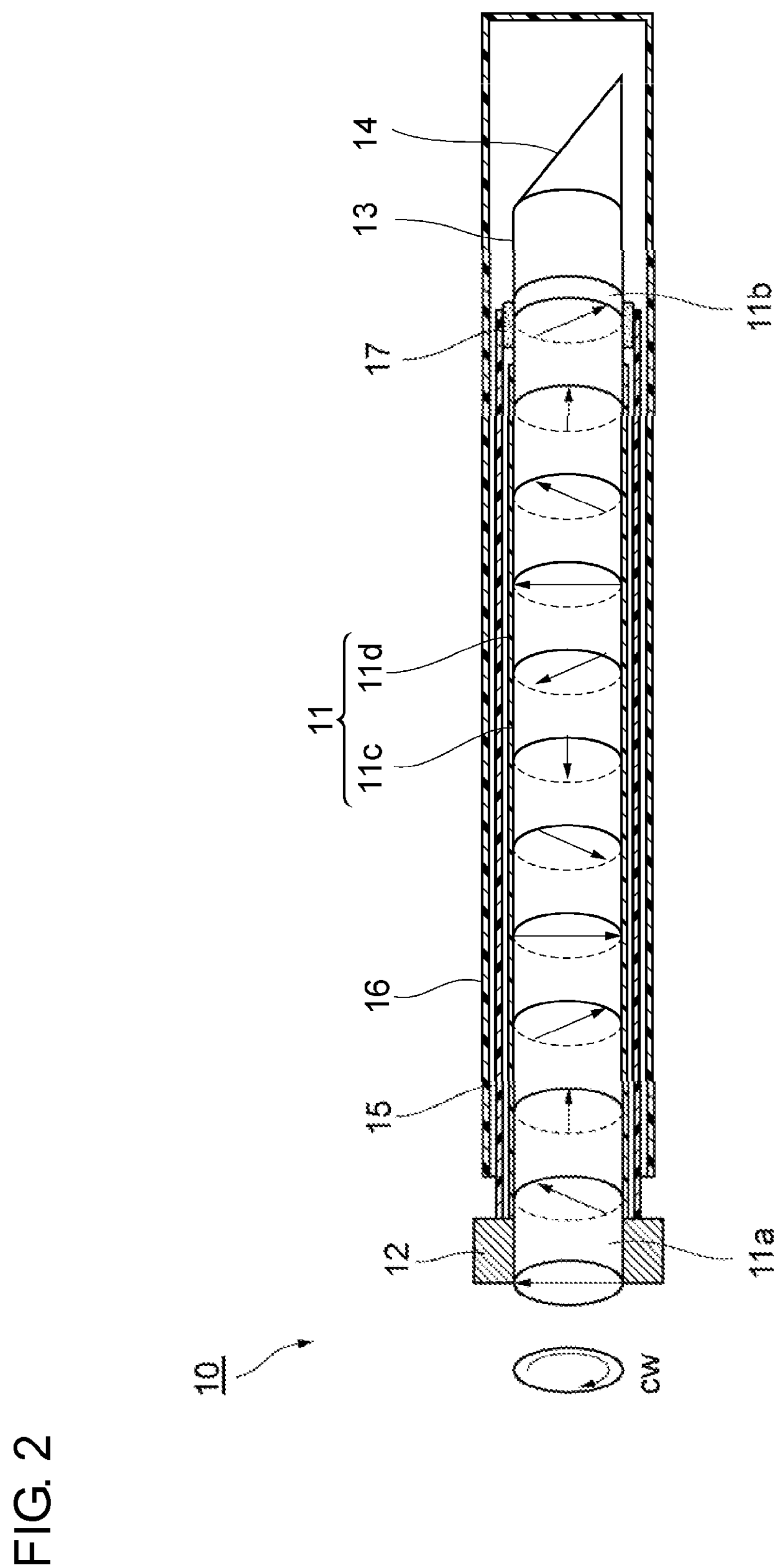
FIG. 2 is a conceptual diagram showing an inner structure of the optical probe according to the embodiment.

FIG. 2 is a conceptual diagram showing an inner structure of the optical probe 10 according to the embodiment. The optical fiber 11 is a typical single-mode optical fiber. The optical fiber has a structure in which a glass fiber 11*c* is covered with a resin coating 11*d*. The glass fiber 11*c* includes a core with high refractive index and a cladding with a low refractive index. The optical fiber 11 is fixed relative to the optical connector 12 at the side of the proximal end 11*a*, and is bonded and fixed to the support tube 15 through an adhesive 17 at the side of the distal end 11*b*. The optical fiber 11 is twisted, and has circular birefringence generated because the optical fiber 11 is twisted. The resin coating 11*d* is removed from a fixed portion with respect to the optical connector 12 and a fixed portion with respect to the support tube 15. The optical connector 12 and the support tube 15 are fixed relative to the glass fiber 11*c*. Accordingly, when the optical connector 12 is rotated, a torque can be efficiently transmitted to the glass fiber 11*c*.

A graded index (GRIN) lens serving as the focusing optical system 13, and a mirror serving as the deflecting optical system 14 are connected in series by fusion splicing at the distal end 11*b* of the optical fiber 11. The focusing optical system 13 focuses the light emitted from the distal end 11*b* of the optical fiber 11. The deflecting optical system 14 deflects the light emitted from the focusing optical system 13 in the radial direction. Alternatively, a GI lens with one end thereof being obliquely cut may form both the focusing optical system 23 and the deflecting optical system 14. The lens (the focusing optical system 13) and the mirror (the deflecting optical system 14) are formed of silica glass or borosilicate glass.

The optical fiber 11 is housed in the inner cavity of the support tube 15. The support tube 15 is bonded and fixed to the optical fiber 11 at the side of the distal end 11*b*, and is fixed relative to the optical connector 12 at the side of the proximal end 11*a*. Consequently, when the optical connector 12 is rotated, the support tube 15 is rotated together. Further, a rotation torque is transmitted to the optical fiber 11, and hence the optical fiber 11, the focusing optical system 13, the deflecting optical system 14, and the support tube 15 are rotated together.

Figure 3:
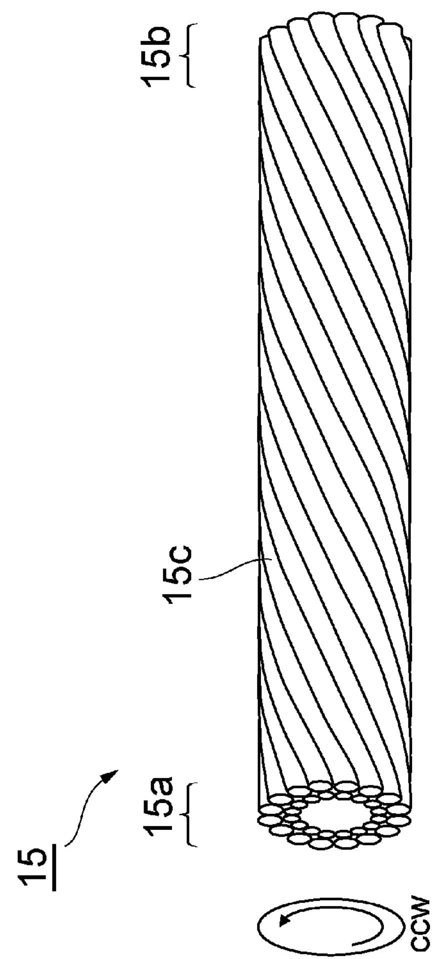
FIG. 3 is a conceptual diagram of a support tube in the optical probe according to the embodiment.

FIG. 3 is a conceptual diagram of the support tube 15 in the optical probe 10 according to the embodiment. The support tube 15 is connected with the optical connector 12 at a side of a proximal end 15*a*, and is connected with the optical fiber 11 at a side of a distal end 15*b*. The support tube 15 has a structure in which a plurality of (typically, 5 to 50) metal wires 15*c* formed of stainless steel, a Co—Cr alloy, or a Ni—Ti alloy are stranded and twisted in a hollow shape. The support tube 15 has a thickness of 0.15 mm or larger, and a Young's modulus in a range from 100 to 300 GPa. Accordingly, the support tube 15 can have flexibility that allows the support tube 15 to be inserted into a soft and bent object, such as a blood vessel. At the same time, the support tube 15 can transmit a rotation torque applied to the side of the proximal end 11*a* efficiently to the side of the distal end 11*b*.

A twist direction of the support tube 15 is defined by a rotation direction when the distal end 11*b* is viewed from the proximal end 11*a* and the viewpoint is moved toward the distal end 11*b*. Also, a rotation direction of the rotation applied to the optical fiber 11 at the proximal end 11*a* during use is defined by a rotation direction of the proximal end 11*a* when the distal end 11*b* is viewed from the proximal end 11*a*. The twist direction of the support tube 15 is a direction opposite to the rotation direction of the rotation applied to the optical fiber 11 at the proximal end 11*a* during use, that is, a direction in which the support tube 15 is twisted more strongly by the rotation.

When the rotation is provided clockwise, a force to move the proximal end 11*a* clockwise relative to the distal end 11*b* is added. The distal end 11*b* is impeded from moving because of the inertia and friction. Accordingly, with this force, the proximal end 11*a* is twisted clockwise relative to the distal end 11*b*. The twist direction at this time is the counterclockwise direction. That is, when the support tube 15, which is twisted counterclockwise, is rotated clockwise, the support tube 15 is twisted more strongly. Accordingly, the support tube 15 can efficiently transmit the rotation torque.

Further, the support tube 15 is preferably formed by stranding metal wires in a form of a plurality of coaxial rings. Accordingly, torque transmitting performance of the support tube 15 can be further increased. In this case, the twist direction of the support tube 15 at the outermost-layer ring is preferably opposite to the direction of the rotation torque during use.

The twist direction and the rotation direction during use of the optical fiber 11 are the clockwise direction (cw direction) (see FIG. 2), and the twist direction of the support tube is the counterclockwise direction (ccw direction) (see FIG. 3) that is opposite to the former direction. Accordingly, when the rotation torque is applied during use, the support tube 15 is further twisted counterclockwise by the rotation torque. The clockwise twist of the optical fiber 11 is restored once and then the optical fiber 11 is twisted counterclockwise.

Consequently, the counterclockwise twist of the optical fiber 11 is decreased by an amount by which the optical fiber 11 is originally twisted clockwise. When the optical probe 10 is rotated at high speed, a large twist is added to the optical fiber 11 by the rotation torque, and hence there is a risk of fracture in which the optical fiber 11 may be broken by the large twist. However, by twisting the optical fiber 11 beforehand in the direction opposite to the direction of the rotation torque, the risk of fracture can be decreased. Alternatively, the twist direction and the rotation direction of the optical fiber 11 may be the counterclockwise direction, and the twist direction of the support tube 15 may be the clockwise direction.

If the optical fiber is twisted, it is known that circular birefringence is generated. As described in R. E. Schuh, Electronics Letters, Vol. 31, No. 20, pp. 1772-1773 (1995), let $\gamma$ be a twist rate (a twist rotation angle per unit length), a propagation constant difference $\Delta\beta t$ by circular birefringence is expressed as follows:

$$\Delta\beta t = g \times \gamma,$$

where a proportionality coefficient g is typically 0.14 in case of glass optical fiber.

Also, if a bend is added to the optical fiber, it is known that linear birefringence is generated at the optical fiber. As described in R. Ulrich, Optics Letters, Vol. 5, No. 6, pp. 273-275 (1980), let r be a glass radius of the optical fiber, and R be a bend radius, a propagation constant difference $\Delta\beta b$ by the linear birefringence is expressed as follows:

$$\Delta\beta b = 0.25 \times n^3 \times k \times \Delta p \times (1+\nu) \times (r/R)^2,$$

where n is a refractive index, k is a wave number, $\Delta p$ is an anisotropy of an optical strain coefficient, and $\nu$ is a Poisson's ratio. In case of glass optical fiber, with a wavelength of 1.3 μm, n=1.447, $\Delta p=-0.15$, and $\nu=0.17$.

When both twist and bend are added to the optical fiber, both circular birefringence and linear birefringence are generated at the optical fiber. At this time, an effect of the larger birefringence becomes dominant. Hence, even though a bend added to the optical fiber may vary depending on the use state, by twisting the optical fiber beforehand to generate the larger birefringence than the linear birefringence caused by the bend, and by entering light in the circular polarization state to the optical fiber, the polarization state of light propagating through the optical fiber can be stably kept. Such a condition can be realized by applying a twist larger than a reference twist rate $\gamma 0$ to the optical fiber. The reference twist rate $\gamma 0$ is given by an equation as follows:

$$\gamma 0 = (0.25/g) \times n^3 \times k \times |\Delta p| \times (1+\nu) \times (r/R)^2.$$

Figure 4:
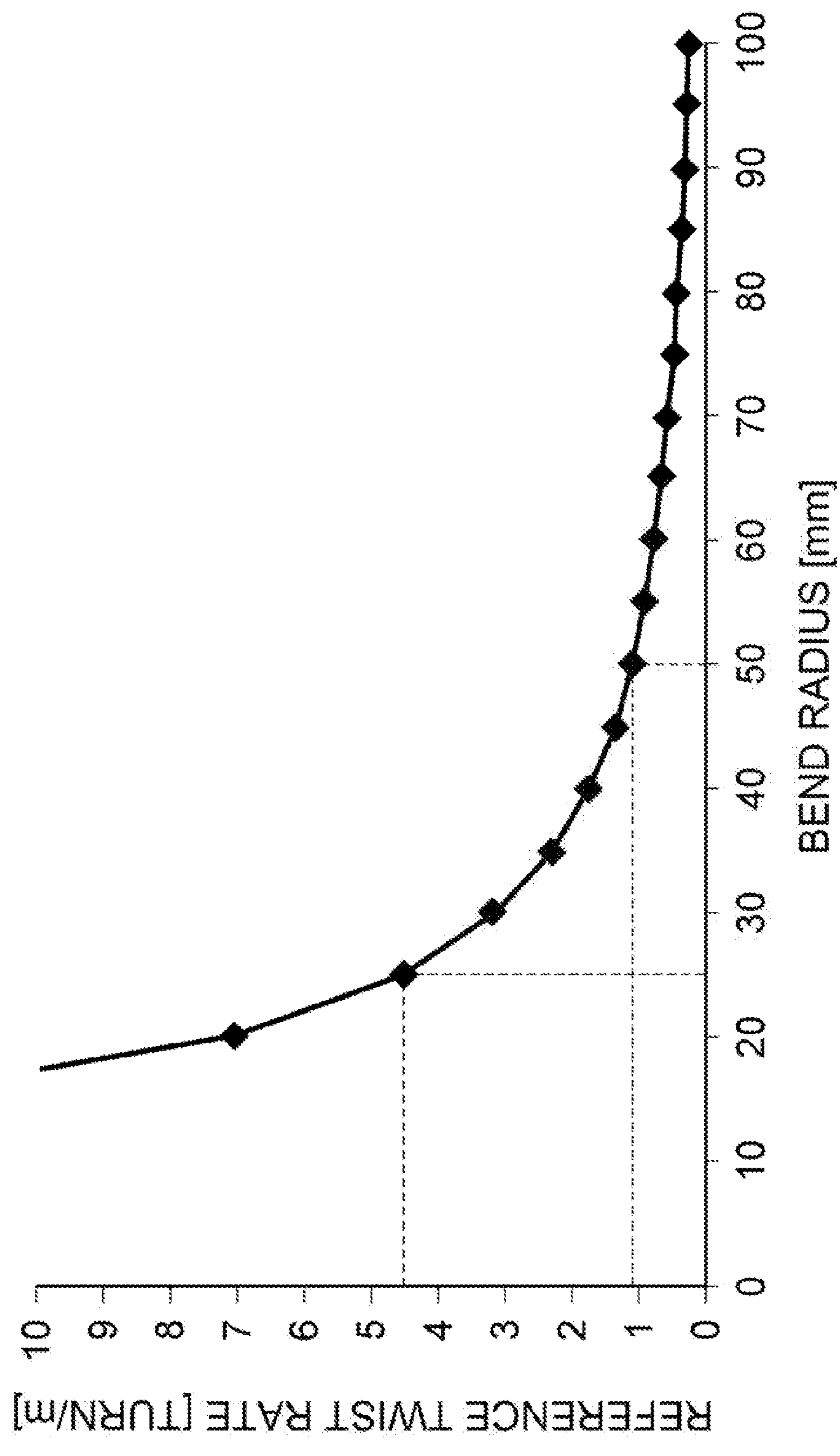
FIG. 4 is a graph showing the relationship between a reference twist rate and a bend radius.

FIG. 4 is a graph showing the relationship between a reference twist rate on the basis of the number of rotations, and a bend radius. In measurement for a blood vessel etc., the optical fiber 11 of the optical probe 10 may typically unavoidably have a bend radius larger than 50 mm, and may occasionally have a bend radius larger than 25 mm. As shown in FIG. 4, the reference twist rate corresponding to the bend radius of 50 mm is 1.1 turns/m, and the reference twist rate corresponding to the bend radius of 25 mm is 4.5 turns/m. Hence, by typically applying a twist of 1 turn/m to the optical fiber 11, the polarization state of the illumination light and the polarization state of the backward reflection light propagating through the optical fiber 11 can be stably kept. Also, by applying a twist of 5 turns/m or more to the optical fiber 11, the polarization state of the illumination light and the polarization state of the backward reflection light can be more likely stably kept.

However, it is also known that the risk of fracture increases if the twist rate is too large. As described in M. Legre, Journal of Lightwave technology, Vol. 21, No. 12, pp. 3374-3378 (2003), since it is known that the risk of fracture increases when the twist rate is 70 to 80 turns/m. To keep the risk of fracture sufficiently low, the twist rate of the optical fiber 11 is preferably 50 times per meter or smaller.

When the optical fiber 11 is rotated for scanning the object 3 with the illumination light, an additional twist because of the rotation torque is added to the optical fiber 11. To perform measurement at high speed, the rotation speed is preferably increased. However, an additional twist is increased accordingly. As described above, in the embodiment, by applying a twist beforehand to the optical fiber 11 in the direction opposite to the direction of an additional twist by the rotation, the absolute value of the twist during rotation is decreased, and hence the risk of fracture of the optical fiber 11 is decreased. More specifically, the twist rate of the optical fiber 11 during rotation is preferably 50 turns/m or smaller. Further, to keep the polarization state of the illumination light and the polarization state of the backward reflection light constant, the twist rate of the optical fiber 11 is preferably 5 turns/m or larger. Also, even when only one portion of the object 3 is measured without rotation, to keep the polarization state of the illumination light and the polarization state of the backward reflection light constant, a twist of one turn/m or more is preferably applied to the optical fiber 11 beforehand.

The invention claimed is:

1. An optical probe, comprising:

an optical fiber that transmits light between a proximal end and a distal end;

an optical connector connected with the optical fiber at a side of the proximal end;

a focusing optical system having one end connected with the optical fiber at the distal end, the focusing optical system focusing the light emitted from the distal end of the optical fiber;

a deflecting optical system optically connected with the optical fiber at a side of the distal end, the deflecting optical system deflecting the light emitted from the distal end of the optical fiber;

a support tube surrounding the optical fiber, extending along the optical fiber, fixed relative to the optical connector at the side of the proximal end, and fixed relative to any of the optical fiber, the focusing optical system, and the deflecting optical system at the side of the distal end; and a jacket tube surrounding the support tube, extending along the support tube, and being rotatable relative to the optical fiber, the optical connector, the focusing optical system, the deflecting optical system, and the support tube, wherein the optical fiber is twisted by a number of turns in a range from 1 turn/m to 50 turns/m around an axis of the optical fiber as the center and fixed relative to the support tube, wherein the support tube has a structure in which a plurality of linear bodies are stranded and twisted, and wherein, in a free state in which rotation is not introduced from the connector, a twist direction of the optical fiber and a twist direction of the support tube are opposite to each other.

2. The optical probe according to claim 1, wherein one end of the deflecting optical system is connected with the other end of the focusing optical system.

3. An optical measurement method implemented with the optical probe according to claim 1, a light source that emits near infrared light, a polarization adjusting part that converts the near infrared light emitted from the light source into near infrared light in a circular polarization state and outputs the near infrared light, an optical branching part that branches the near infrared light output from the polarization adjusting part into two of illumination light and reference light and outputs the illumination light and the reference light, an optical detector that detects the near infrared light, and an analyzing part that analyzes an attenuation spectrum of the near infrared light and acquires the analysis result as image information; the method comprising;

irradiating an object with the illumination light which is output from the optical branching part, entered to the proximal end of the optical fiber, and emitted from the distal end of the optical fiber;

guiding backward reflection light which is generated at the object as the result of the irradiation to the optical detector by causing the backward reflection light entered to the distal end of the optical fiber and emitted from the proximal end of the optical fiber, while guiding the reference light output from the optical branching part to the optical detector, detecting interference light of the backward reflection light and the reference light by the optical detector; and analyzing a spectrum of the backward reflection light by the analyzing part and acquiring distribution information of a substance in the object as the image information.

4. The optical measurement method according to claim 3, wherein the inside of the object is scanned with the illumination light while the optical fiber, the optical connector, the focusing optical system, the deflecting optical system, and the support tube are rotated together in a direction opposite to the twist direction of the support tube.

5. The optical measurement method according to claim 3, wherein the optical fiber is twisted by a number of turns in a range from 5 turns/m to 50 turns/m by rotating the optical fiber, the optical connector, the focusing optical system, the deflecting optical system, and the support tube together.

* * * * *